(12) United States Patent
Omura et al.

(10) Patent No.: US 7,968,706 B2
(45) Date of Patent: Jun. 28, 2011

(54) METHOD OF MANUFACTURING PHTHALOCYANINE COMPOUND

(75) Inventors: Kazufumi Omura, Kanagawa (JP); Shingo Satoh, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 379 days.

(21) Appl. No.: 12/160,500

(22) PCT Filed: Jan. 23, 2007

(86) PCT No.: PCT/JP2007/051330
§ 371 (c)(1),
(2), (4) Date: Jul. 10, 2008

(87) PCT Pub. No.: WO2007/086537
PCT Pub. Date: Aug. 2, 2007

(65) Prior Publication Data
US 2010/0240885 A1    Sep. 23, 2010

(30) Foreign Application Priority Data

Jan. 24, 2006   (JP) .................................. 2006-014560
Sep. 13, 2006   (JP) .................................. 2006-248318

(51) Int. Cl.
*C07B 47/00* (2006.01)
*C07D 487/22* (2006.01)
(52) U.S. Cl. ...................................................... 540/145
(58) Field of Classification Search .................... 540/145
See application file for complete search history.

(56) References Cited

FOREIGN PATENT DOCUMENTS

| JP | 38-17479 | B1 | 9/1963 |
| JP | 6-192583 | A | 7/1994 |
| JP | 2006-124379 | A | 5/2006 |
| JP | 2006-124679 | A | 5/2006 |

OTHER PUBLICATIONS

McKeown "Product Class 9: . . . ", Science of Synthesis, vol. 17, Jan. 1, 2004, pp. 1237-1368.*
Extended European Search Report dated Mar. 23, 2010 on EP Application No. 07707561.2.
N. B. McKeown, "Product Class 9: Phthalocyanines and Related Compounds", Science of Synthesis, vol. 17, Jan. 1, 2004, pp. 1237-1368. XP009050738.

* cited by examiner

*Primary Examiner* — Paul V. Ward
(74) *Attorney, Agent, or Firm* — Sughrue Mion, PLLC

(57) ABSTRACT

Provided is a method of manufacturing a phthalocyanine compound denoted by general formula (3). The method comprises conducting a reaction of a compound denoted by general formula (1) or (2) with a metal and/or metal compound in a solvent in the presence of a secondary amine and/or diamine to obtain the phthalocyanine compound denoted by general formula (3).

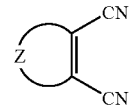

General formula (1)

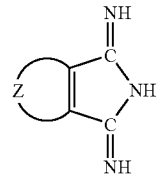

General formula (2)

In general formulas (1) and (2), Z denotes an organic group forming a six-membered cyclic aromatic structure with two carbon atoms bonded to Z.

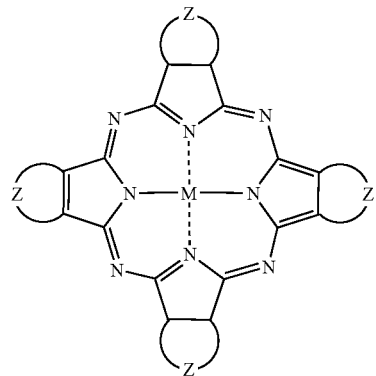

General formula (3)

In general formula (3), Z is one defined as in general formulas (1) and (2), and M denotes a metal atom belonging to Periods 1 to 4 of Groups 1 to 12.

10 Claims, No Drawings

METHOD OF MANUFACTURING PHTHALOCYANINE COMPOUND

CROSS-REFERENCE TO RELATED APPLICATIONS

This application claims benefit of priority under 35 USC 119 to Japanese Patent Application No. 2006-014560 filed on Jan. 24, 2006 and Japanese Patent Application No. 2006-248318 filed on Sep. 13, 2006, which are expressly incorporated herein by reference in their entirety.

BACKGROUND OF THE INVENTION

1. Field of the Invention

The invention relates to a method of manufacturing a phthalocyanine compound.

2. Discussion of the Background

Phthalocyanine compounds and their analogs are widely employed as dyes and pigments exhibiting high fastness as well as functional coloring materials. The synthesis of phthalocyanine compounds is widely known. One example is a method in which the reaction is conducted in a high-boiling-point alcohol (n-butanol or the like) solvent in the presence of a strong base such as DBU (1,8-Diazabicyclo[5.4.0]undec-7-ene) (see Japanese Unexamined Patent Application (KOKAI) Heisei No. 11-269399, or English language family member U.S. Pat. Nos. 5,973,140 and 6,093,832, which are expressly incorporated herein by reference in their entirety). Another is a method employing a metal alkoxide (see Japanese Unexamined Patent Application (KOKAI) Heisei No. 11-209380, which is expressly incorporated herein by reference in its entirety). However, in these methods, the reaction system becomes highly alkaline, precluding the use of matrixes having substituents that tend to decompose under alkaline conditions.

Accordingly, methods of conducting a reaction in the presence of a disilazane such as hexamethyl disilazane with a dimethylformamide solvent (see Japanese Unexamined Patent Application (KOKAI) Nos. 2002-226482 and 2004-26693, which are expressly incorporated herein by reference in their entirety) have been proposed as methods of synthesizing phthalocyanine compounds without employing a strong base. However, problems such as the high cost of disilazanes remain in industrial applications.

In addition, phthalocyanine compounds have large ring structures formed by coordinate bonds between a center metal and four nitrogen atoms surrounding the center metal. Therefore, there is a problem in the synthesis of phthalocyanine compounds in that reactivity varies greatly with the nitrogen affinity of the center metal.

SUMMARY OF THE INVENTION

A feature of the present invention provides for a method of manufacturing phthalocyanine compounds comprising a desired metal as a center metal.

The present inventors conducted extensive research and discovered that by preparing a center metal as a metal complex to activate it, a phthalocyanine compound containing a desired metal as a center metal could be obtained at high efficiency irrespective of the nitrogen affinity of the center metal; the present invention was devised on this basis.

A feature of the present invention relates to a method of manufacturing a phthalocyanine compound denoted by general formula (3), which comprises conducting a reaction of a compound denoted by general formula (1) or (2) with a metal and/or metal compound in a solvent in the presence of a secondary amine and/or diamine to obtain the phthalocyanine compound denoted by general formula (3).

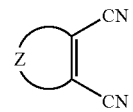

General formula (1)

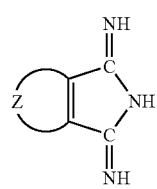

General formula (2)

In general formulas (1) and (2), Z denotes an organic group forming a six-membered cyclic aromatic structure with two carbon atoms bonded to Z.

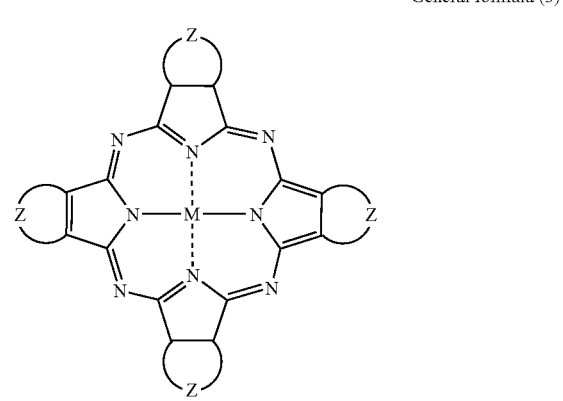

General formula (3)

In general formula (3), Z is one defined as in general formulas (1) and (2), and M denotes a metal atom belonging to Periods 1 to 4 of Groups 1 to 12.

Based on the present invention, a phthalocyanine compound comprising a desired metal as a center metal can be readily produced at high yield regardless of the nitrogen affinity of the center metal.

Further, based on the present invention, since it is unnecessary to conduct the reaction under highly alkaline conditions, phthalocyanine compounds having various substituents can be efficiently synthesized.

Other exemplary embodiments and advantages of the present invention may be ascertained by reviewing the present disclosure.

DESCRIPTIONS OF THE EMBODIMENTS

The following preferred specific embodiments are, therefore, to be construed as merely illustrative, and not limitative of the remainder of the disclosure in any way whatsoever. In this regard, no attempt is made to show structural details of the present invention in more detail than is necessary for the fundamental understanding of the present invention, the description taken with the drawings making apparent to those skilled in the art how the several forms of the present invention may be embodied in practice.

The method of manufacturing a phthalocyanine compound of the present invention is a method of manufacturing a phthalocyanine compound denoted by general formula (3). In this method, the phthalocyanine compound denoted by general formula (3) is manufactured by conducting a reaction of a phthalonitrile derivative denoted by general formula (1) or a pyrrole-2,5-diylidenediamine compound denoted by general formula (2) with a metal and/or metal compound in a solvent in the presence of a secondary amine and/or diamine.

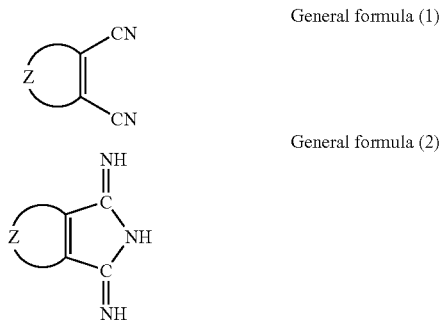

General formula (1)

General formula (2)

In general formulas (1) and (2), Z denotes an organic group forming a six-membered cyclic aromatic structure with two carbon atoms bonded to Z. The aromatic structure may be monocyclic or a condensed structure obtained by ring fusion. The aromatic structure of the six-membered ring formed by Z and the carbon atoms bonded to Z may be an alicyclic structure such as a benzene ring or naphthalene ring, or a nitrogen-containing aromatic heterocyclic structure such as a pyridine ring, pyrazine ring, pyridazine ring, pyrimidine ring, triazine ring, quinoline ring, or phthalazine ring. The aromatic structure is preferably a benzene ring, naphthalene ring, pyridine ring, or pyridazine ring, more preferably a benzene ring, naphthalene ring, or pyridine ring, and further preferably, a benzene ring. The aromatic structure may be substituted. Specific examples of substituents are those that can be included in the phthalonitrile compound of general formula (4), described further below. The pyrrole-2,5-diylidenediamine compound denoted by general formula (2) may be employed in the form denoted by general formula (2), or in the form of a tautomer thereof.

The compound denoted by general formula (1) is desirably employed in the form of the compound denoted by general formula (4) below.

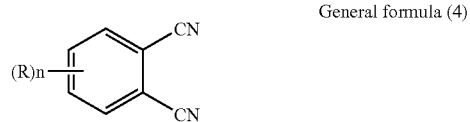

General formula (4)

In general formula (4), R denotes a hydrogen atom or a substituent. Specific examples of substituents are: halogen atoms (for example, a fluorine atom, chlorine atom, bromine atom, or iodine atom); an alkyl group (straight or branched chain, optionally substituted alkyl group (desirably having 1 to 30 carbon atoms) such as a methyl group, ethyl group, n-propyl group, isopropyl group, t-butyl group, n-octyl group, eicosyl group, 2-chloroethyl group, 2-cyanoethyl group, 2-ethylhexyl group, or 3-(2,4-di-t-amyl-phenoxy)propyl group); aralkyl group (desirably an optionally substituted aralkyl group having 7 to 30 carbon atoms such as a benzyl group or phenethyl group); cycloalkyl group (desirably an optionally substituted cycloalkyl group having 3 to 30 carbon atoms such as a cyclohexyl group, cyclopentyl group, or 4-n-dodecylcyclohexyl group); alkenyl group (optionally substituted straight chain or branched chain alkenyl group (desirably having 2 to 30 carbon atoms) such as a vinyl group, allyl group, prenyl group, geranyl group, or oleyl group); cycloalkenyl group (desirably an optionally substituted cycloalkenyl group having 3 to 30 carbon atoms such as a 2-cyclopentene-1-yl or 2-cyclohexene-1-yl); alkynyl group (optionally substituted straight chain or branched chain alkynyl group (desirably having 2 to 30 carbon atoms) such as an ethynyl group, propagyl group, or trimethylsilylethynyl group); aryl group (an optionally substituted aryl group having 6 to 30 carbon atoms, such as a phenyl group, p-tolyl group, naphthyl group, m-chlorophenyl group, o-hexadecanoylaminophenyl group); heterocyclic group (desirably a five to seven-membered, optionally substituted, saturated or unsaturated, aromatic or nonaromatic, monocyclic or condensed heterocyclic group, preferably a heterocyclic group in which the atoms comprising the ring are selected from among carbon, nitrogen, and sulfur atoms, having at least one heteroatom from among nitrogen atoms, oxygen atoms, and sulfur atoms, more preferably a five or six-membered aromatic heterocyclic group having 3 to 30 carbon atoms (such as a 2-furyl group, 2-thienyl group, 2-pyridyl group, 4-pyridyl group, 2-pyrimidinyl group, or 2 benzothiazolyl group), and still more preferably a heterocyclic group comprising a quaternized nitrogen atom (such as a pyridinio group, imidazolio group, quinolinio group, or isoquinolinio group));

acyl group (desirably a formyl group, optionally substituted alkylcarbonyl group having 2 to 30 carbon atoms or an optionally substituted arylcarbonyl group having 7 to 30 carbon atoms such as an acetyl group, pivaloyl group, 2-chloroacetyl group, stearoyl group, benzoyl group, or p-n-octyloxyphenylcarbonyl group); alkoxycarbonyl group (desirably an optionally substituted alkoxycarbonyl group having 2 to 30 carbon atoms, such as a methoxycarbonyl group, ethoxycarbonyl group, t-butoxycarbonyl group, or n-octadecyloxycarbonyl group); aryloxycarbonyl group (desirably an optionally substituted aryloxycarbonyl group having 7 to 30 carbon atoms such as a phenoxycarbonyl group, o-chlorophenoxycarbonyl group, m-nitrophenoxycarbonyl group, or p-t-butylphenoxycarbonyl group); carbamoyl group (desirably an optionally substituted carbamoyl group having 1 to 30 carbon atoms such as a carbamoyl group, N-methylcarbamoyl group, N,N-dimethylcarbamoyl group, N,N-di-n-octylcarbamoyl group, or N-(methylsulfonyl)carbamoyl group); carboxy group or salt thereof; sulfonylcarbamoyl group (such as an optionally substituted sulfonylcarbamoyl group having 2 to 30 carbon atoms such as a methanesulfonylcarbamoyl group, octanesulfonylcarbamoyl group, or benzenesulfonylcarbamoyl group);

acylcarbamoyl group (desirably an acylcarbamoyl group having 2 to 30 carbon atoms such as a formylcarbamoyl group, methylcarbamoyl group, phenylcarbamoyl group); sulfamoylcarbamoyl group (desirably a sulfamoylcarbamoyl group having 1 to 30 carbon atoms such as a methylsulfamoylcarbamoyl group or phenylsulfamoylcarbamoyl group); carbazoyl group (desirably a 1 to 30 carbazoyl group such as a carbazoyl group, 3-ethylcarbazoyl group, 3,3-dimethylcarbazoyl group, or 2-ethyl-3-phenylcarbazoyl group); oxalyl group (desirably an oxalyl group having 2 to 30 carbon atoms such as a methyloxalyl group, phenyloxalyl group, ethoxyoxalyl group, or phenoxyoxalyl group); oxamoyl group (desirably an oxamoyl group having 2 to 30 carbon atoms such as an oxamoyl group, N-ethyloxamoyl group, N-phenyloxamoyl group, or N,N-diethyloxamoyl group); cyano group, thiocarbamoyl group (desirably a thiocarbamoyl group having 1 to 30 carbon atoms such as a thiocarbamoyl group, N-ethylthiocarbamoyl group, or N-phenylthiocarbamoyl group); hydroxy group, alkoxy group (comprising a repeating ethyleneoxy group or propyleneoxy group unit, desirably an alkoxy group having 1 to 30 carbon atoms such as a methoxy group, ethoxy group, octyloxy group. or hexadecyloxy group);

aryloxy group (desirably an optionally substituted aryloxy group having 6 to 30 carbon atoms such as a phenyloxy group or naphthyloxy group); heterocyclic oxy group (the heterocyclic oxy groups among the above-listed heterocyclic groups being desirable, such as a pyridyloxy group, imidazoyloxy group, or piperidyloxy group); acyloxy group (desirably an acyloxy group having from 1 to 30 carbon atoms such as a formyloxy group, acetyloxy group, or benzoyloxy group); alkoxy or aryloxy carbonyloxy group (desirably an alkoxycarbonyloxy group having 1 to 30 carbon atoms or an aryloxycarbonyloxy having 6 to 30 carbon atoms such as methoxycarbonyloxy or phenoxycarbonyloxy); carbamoyloxy group (desirably a carbamoyloxy group having 1 to 30 carbon atoms, ethylcarbamoyloxy group, or phenylcarbamoyloxy group); sulfonyloxy group (desirably a sulfonyloxy group having 2 to 30 carbon atoms such as a methanesulfonyloxy group or benzenesulfonyloxy group);

amino group; alkyl, aryl, or heterocyclic amino group (desirably an alkylamino group in which the alkyl moiety has 1 to 30 carbon atoms, an arylamino group in which the aryl moiety has 6 to 30 carbon atoms, or a heterocyclic amino group in which the heterocyclic moiety is one of those set forth above) such as a methylamino group, diethylamino group, phenylamino group, or pyridylamino group); acylamino group (desirably an acylamino group having 1 to 30 carbon atoms such as a formylamino group, acetylamino group, or benzoylamino group); sulfonamide group (desirably a sulfonamide group having 1 to 30 carbon atoms such as an ethanesulfonamide group or benzene sulfonamide group); ureido group (desirably an ureido group having 1 to 30 carbon atoms such as a ureido group, methylureido group, or phenylureido group); thioureido group (desirably a thioureido group having 1 to 30 carbon atoms such as a methylthioureido group or phenylthioureido group); imido group (desirably an optionally substituted ureido group having 2 to 30 carbon atoms such as an N-succinimide group or N-phthalimide group);

(alkoxy or aryloxy)carbonylamino group (desirably an alkoxycarbonylamino group having 2 to 30 carbon atoms or an aryloxycarbonylamino group having 7 to 30 carbon atoms such as a methoxycarbonylamino group or phenoxycarbonylamino group); sulfamoylamino group (desirably a sulfamoylamino group having 1 to 30 carbon atoms such as a methanesulfamoylamino group or benzenesulfamoylamino group); semicarbazide group (desirably a semicarbazide group having 1 to 30 carbon atoms such as a semicarbazide group, N-ethylsemicarbazide group, or N-phenylsemicarbazide group); thiosemicarbazide group (desirably a thiosemicarbazide group having 1 to 30 carbon atoms such as a thiosemicarbazide group, N-butylthiosemicarbazide group, or N-phenylthiosemicarbazide group); hydrazino group (desirably a hydrazino group having 1 to 30 carbon atoms such as a hydrazino group, ethylhydrazino group, or phenylhydrazino group); ammonio group; oxamoylamino group (desirably an oxamoylamino group having 2 to 30 carbon atoms such as an oxamoyl group, ethyloxamoyl group, or phenyloxamoyl group); alkyl or aryl sulfonylureido group (desirably an alkylsulfonylureido group having 2 to 30 carbon atoms or an arylsulfonylureido group having 7 to 30 carbon atoms such as a methanesulfonylureido group or benzenesulfonylureido group); acylureido group (desirably an acylureido group having 2 to 30 carbon atoms such as a formylureido group, acetylureido group, or benzoylureido group); acylsulfamoylamino group (desirably an acylsulfamoylamino group having 1 to 30 carbon atoms such as an acetylsulfamoylamino group or benzoylsulfamoylamino group), nitro group, or mercapto group;

alkyl, aryl, or heterocyclic thio group (desirably an alkylthio group in which the alkyl moiety has 1 to 30 carbon atoms, an arylthio group in which the aryl moiety has 6 to 30 carbon atoms, or a heterocyclic thio group in which the heterocyclic moiety is one of those given above) such as a methylthio, phenylthio, or pyridinylthio; an alkyl, aryl, or heterocyclic sulfonyl group (desirably an alkylsulfonyl group in which the alkyl moiety has 1 to 30 carbon atoms, an arylsulfonyl group in which the aryl moiety has 6 to 30 carbon atoms, or a heterocyclic sulfonyl group in which the heterocyclic moiety is one of those given above) such as a methylsulfonyl, phenylsulfonyl, or pyridylsulfonyl; an alkyl, aryl, or heterocyclic sulfinyl group (desirably an alkylsulfinyl group in which the alkyl moiety has 1 to 30 carbon atoms, an arylsulfinyl group in which the aryl moiety has 6 to 30 carbon atoms, or a heterocyclic sulfinyl group in which the heterocyclic moiety is one of those given above) such as a methylsulfinyl, phenylsulfinyl, or pyridylsulfinyl; sulfo group or salt thereof; sulfamoyl group (such as a sulfamoyl group having 0 to 30 carbon atoms such as a sulfamoyl, ethanesulfamoyl, or benzenesulfamoyl); acylsulfamoyl group (desirably an acylsulfamoyl group having 1 to 30 carbon atoms such as a formylsulfamoyl, acetylsulfamoyl, or benzoylsulfamoyl); sulfonylsulfamoyl group or salt thereof (desirably having 0 to 30 carbon atoms, such as a methanesulfonylsulfamoyl or benzenesulfonylsulfamoyl); a group comprising a phosphoric amide or phosphoric ester structure (desirably having 0 to 30 carbon atoms such as phosphoric amide, methylphosphoric amide, phenylphosphoric amide, ethoxyphosphoric amide, or phenoxyphosphoric amide); silyloxy group (desirably a silyloxy group having 1 to 30 carbon atoms such as trimethylsilyloxy or t-butyldimethylsilyloxy); or a silyl group (desirably a silyl group having 1 to 30 carbon atoms such as a trimethylsilyl, t-butyldimethylsilyl, or phenyldimethylsilyl).

When R denotes a substituent, R is preferably a halogen atom, alkyl group, alkenyl group, alkynyl group, aryl group, heterocyclic group, acyl group, alkoxycarbonyl group, carbamoyl group, carboxy group or salt thereof, oxalyl group, oxamoyl group, cyano group, hydroxy group, alkyloxy group, aryloxy group, heterocyclic oxy group, sulfonyloxy group, alkylamino group, arylamino group, heterocyclic amino group, acylamino group, sulfonamide group, mercapto group, alkylthio group, arylthio group, heterocyclic thio group, alkylsulfonyl group, arylsulfonyl group, heterocyclic sulfonyl group, alkylsulfinyl group, arylsulfinyl group, heterocyclic sulfinyl group, sulfo group or salt thereof, sulfamoyl group, or group having a phosphoric amide or phosphoric ester structure.

More preferably, R denotes a halogen atom, alkyl group, aryl group, heterocyclic group, acyl group, carbamoyl group, carboxy group or salt thereof, oxamoyl group, alkyloxy group, aryloxy group, heterocyclic group, alkylamino group, arylamino group, heterocyclic amino group, acylamino group, sulfonamide group, alkylthio group, arylthio group, heterocyclic thio group, alkylsulfonyl group, arylsulfonyl group, heterocyclic sulfonyl group, alkylsulfinyl group, arylsulfinyl group, heterocyclic sulfinyl group, sulfo group or salt thereof, or sulfamoyl group.

Further preferably, R denotes a halogen atom, alkyl group, aryl group, heterocyclic group, acyl group, carbamoyl group, oxamoyl group, alkyloxy group, aryloxy group, heterocyclic oxy group, alkylamino group, arylamino group, heterocyclic amino group, acylamino group, sulfonamide group, alkylthio group, arylthio group, heterocyclic thio group, alkylsulfonyl group, arylsulfonyl group, heterocyclic sulfonyl group, or sulfamoyl group.

Still more preferably, R denotes an alkoxy group, aryloxy group, heterocyclic oxy group, alkylsulfonyl group, arylsulfonyl group, heterocyclic sulfonyl group, alkylthiol group, arylthiol group, heterocyclic thiol group, or sulfamoyl group. Of these, a sulfonyl group is preferred, with an alkylsulfonyl group having 1 to 4 carbon atoms being further preferred.

The substituent denoted by R may be further substituted. The substituted substituent includes substituents substituted with any other substituent, with substituents substituted with hydrophilic groups being preferred. Specific examples are substituents substituted with hydrophilic groups such as carboxyl groups, sulfo groups, phosphoric acid groups, groups having a quaternary salt structure with nitrogen, or groups having a quaternary salt structure with phosphorus. When the hydrophilic group is a carboxyl group, sulfo group, or phosphoric acid group, it may have a paired cation as needed. Examples of the paired cation are a metal ion, a group having a quaternary salt structure with nitrogen, and a group having a quaternary salt structure with phosphorus. When the substituent is substituted with a hydrophilic group in the form of a group having a quaternary salt structure with nitrogen or a quaternary salt structure with phosphorus, it may have a paired cation as needed. Examples of paired cations are halogen ions, sulfuric acid ions, nitric acid ions, phosphoric acid ions, oxalic acid ions, alkanesulfonic acid ions, arylsulfonic acid ions, alkanecarboxylic acid ions, and arylcarboxylic acid ions.

Hydrophilic groups are preferably carboxyl groups, sulfo groups, and phosphoric acid groups. Hydrophilic groups are more preferably carboxyl groups and sulfo groups. In this case, the paired cation is preferably a cation of Li, Na, K, Mg, or Ca cation, more preferably a action of Li, Na, or K, and further preferably, a cation of Li or Na.

When R is a group having carbon atoms, the total number of carbon atoms is desirably from 1 to 100, more preferably from 1 to 80, further preferably from 1 to 50, and still more preferably from 1 to 20.

In general formula (4), n denotes an integer of 1 to 4; n is preferably from 1 to 3, more preferably 1 or 2. When n is 2 to 4, plural Rs are present. In such cases, the plural Rs may be identical to or different from each other. The plural Rs may also be bonded in a ring configuration.

In the synthesis of a phthalocyanine compound from the phthalonitrile compound denoted by general formula (4), four molecules of phthalonitrile compound are required per molecule of phthalocyanine compound. In this case, in the phthalonitrile compound denoted by general formula (4), the necessary four molecules do not necessarily have to be identical; multiple types of phthalonitriles having different Rs may be employed in any desired ratio.

The substitution position of R in the phthalonitrile compound of general formula (4) may be any position at which substitution is possible. Substitution at the ortho position of the cyano group, that is, the third or sixth position, or the fourth or fifth position, is desirable.

Specific examples of phthalonitrile compounds denoted by general formula (4) suitable for use in the present invention will be given below. However, the present invention is not limited thereto.

TABLE 1

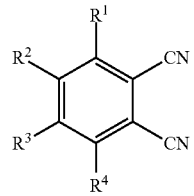

| Compound | $R^1$ | $R^2$ | $R^3$ | $R^4$ |
|---|---|---|---|---|
| 1 | —OEt | H | H | H |
| 2 | —S-$^n$Bu | H | H | H |
| 3 | —SO-$^n$Bu | H | H | H |
| 4 | —SO$_2$-$^n$Bu | H | H | H |
| 5 | —SO$_2$—(CH$_2$)$_3$—SO$_3$Na | H | H | H |
| 6 | —SO$_2$—(CH$_2$)$_3$—SO$_3$Li | H | H | H |
| 7 | —SO$_2$—(CH$_2$)$_3$—SO$_2$NH$_2$ | H | H | H |
| 8 | —S—Ph | H | H | H |
| 9 | —SO$_2$—Ph | H | H | H |
| 10 | —SO$_2$—(CH$_2$)$_3$—CO$_2$Et | H | H | H |
| 11 | —SO$_2$—(CH$_2$)$_4$—SO$_3$Na | H | H | H |
| 12 | —SO$_2$—(CH$_2$)$_2$—SO$_3$Na | H | H | H |
| 13 | —SO$_2$—(CH$_2$)$_5$—SO$_3$Li | H | H | H |
| 14 | —SO$_2$—CH$_2$CH$_2$—O—CH$_2$CH$_2$—SO$_3$Na | H | H | H |
| 15 | —SO$_2$—CH$_2$CH$_2$—(O—CH$_2$CH$_2$)$_2$—SO$_3$Na | H | H | H |
| 16 | —SO$_2$—CH$_2$CH$_2$—(O—CH$_2$CH$_2$)$_3$—SO$_3$Na | H | H | H |
| 17 | —SO$_2$—CH$_2$CH$_2$—(O—CH$_2$CH$_2$)$_4$—SO$_3$Na | H | H | H |
| 18 | —SO$_2$—CH$_2$CH$_2$—(O—CH$_2$CH$_2$)$_5$—SO$_3$Na | H | H | H |
| 19 | H | —OEt | H | H |
| 20 | H | —S-$^n$Bu | H | H |
| 21 | H | —CONH$_2$ | H | H |

TABLE 1-continued

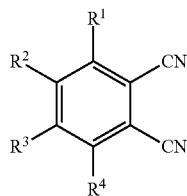

| Compound | R¹ | R² | R³ | R⁴ |
|---|---|---|---|---|
| 22 | H | —SO$_2$NHPh | H | H |
| 23 | H | —SO$_2$—(CH$_2$)$_3$—SO$_3$Li | H | H |
| 24 | H | —SO$_2$—(CH$_2$)$_3$—SO$_3$NH$_2$ | H | H |
| 25 | H | —S—C$_6$H$_4$—CO$_2$Et | H | H |
| 26 | H | —S-(3-Py) | H | H |
| 27 | H | —SO$_2$—(CH$_2$CH$_2$O)$_4$—H | H | H |
| 28 | H | —SO$_2$—(CH$_2$)$_4$—SO$_3$Na | H | H |
| 29 | —OEt | H | H | —OEt |
| 30 | —S-$^n$Bu | H | H | —S-$^n$Bu |
| 31 | —SO$_2$NHPh | H | H | H |
| 32 | —S—(CH$_2$)$_3$—SO$_3$Na | H | H | H |
| 33 | —SO$_2$—(CH$_2$)$_3$—SO$_3$K | H | H | H |
| 34 | —O-$^i$Pr | H | H | —O-$^i$Pr |
| 35 | H | —O-$^n$Bu | —O-$^n$Bu | H |
| 36 | H | —S-$^n$Hex | Cl | H |
| 37 | H | —O—(CH$_2$CH$_2$O)$_5$—H | —O—(CH$_2$CH$_2$O)$_5$—H | H |
| 38 | —CO—Ph | H | H | H |
| 39 | —SO$_2$-$^s$Bu | H | H | H |
| 40 | —S—C$_6$H$_4$—C(=O)N(CH$_2$CH$_2$OC$_2$H$_5$)$_2$ | H | H | H |
| 41 | —S—C$_6$H$_4$—C(=O)N(CH$_2$CH$_2$OCH$_3$)$_2$ | H | H | H |
| 42 | —S—C$_6$H$_4$—C(=O)N(CH$_2$CH$_2$OC$_2$H$_5$)(CH(CH$_3$)COOH) | H | H | H |
| 43 | —S—C$_6$H$_4$—C(=O)N(CH$_2$CH$_2$OC$_2$H$_4$OC$_2$H$_5$)(CH$_2$CH$_2$COOH) | H | H | H |
| 44 | —S—C$_6$H$_4$—C(=O)N(CH$_2$CH$_2$OC$_2$H$_4$OC$_2$H$_5$)(CH$_2$CH$_2$CH$_2$SO$_3$Na) | H | H | H |
| 45 | —S—C$_6$H$_4$—CO$_2$Et | H | H | H |

In Table 1, "Et" denotes an ethyl group, "Bu" denotes a butyl group, "Hex" denotes a hexyl group, "Ph" denotes a phenyl group, "Pr" denotes a propyl group, and "Py" denotes a pyridyl group.

In the present invention, the compound denoted by general formula (1) or (2) is reacted with a metal and/or metal compound (also referred as a "metal component" hereinafter) to obtain the phthalocyanine compound denoted by general formula (3). The metal atom contained in the metal or metal compound belongs to Periods 1 to 4 of Groups 1 to 12 of the Long form of Periodic Table of the Elements, namely: Li, Be, Na, Mg, K, Ca, Sc, Ti, V, Cr, Mn, Fe, Co, Ni, Cu, or Zn. More specifically, it belongs to Periods 2 to 3 of Groups 1 to 12, namely Li, Be, Na, Mg, or Period 4 of Groups 7 to 12, namely Mn, Fe, Co, Ni, Cu, and Zn. It may be selected based on the center metal of the desired phthalocyanine compound.

According to the present invention, a phthalocyanine compound having a desired center metal can be obtained at high yield without being effected by differences in the nitrogen affinity (reactivity) of the center metal. The method of manufacturing a phthalocyanine compound of the present invention is suited to the manufacturing of phthalocyanine compounds containing a center metal in the form of copper, a metal of particularly high nitrogen affinity among the metals.

It is also suited to the manufacturing of phthalocyanine compounds containing center metals with lower nitrogen affinity than copper. Since phthalocyanine compounds having such metals as center metals have low reactivity due to their nitrogen affinity, they have been previously considered difficult to synthesize. By contrast, according to the present invention, phthalocyanine compounds containing desired metals as center metals can be obtained without being affected by nitrogen affinity. Examples of such metals are Mn, Fe, Co, Ni, Mg, and Zn.

Oxides, hydroxides, halides, acetates, and sulfates of the above-listed metals may be employed as the metal compounds. Specific examples of the above metal compounds are: $MnCl_2$, $FeCl_3$, $CoCl_2$, $NiCl_2$, $CuCl_2$, $MgBr_2$, and $ZnBr_2$. The quantity employed can be equal to or greater than 0.20 mole, preferably 0.25 to 1 mole, per mole of the phthalonitrile derivative denoted by general formula (1) or the pyrrole-2,5-diylidenediamine compound denoted by general formula (2) that is employed as starting material.

The reaction is conducted in the presence of a secondary amine and/or diamine (also referred to as an "amine" hereinafter).

These amines are thought to form a complex with a metal component in a solvent. When in the form of such a complex, the reactivity of the starting compound of general formula (1) or (2) improves relative to when the reaction is conducted in the presence of the metal component itself. Thus, even for metals of relatively low affinity with nitrogen, good coordinate bonds with the nitrogen contained in the above starting compounds are thought to form. Thus, based on the present invention, a phthalocyanine compound having a center metal in the form of a desired metal can be obtained at high yield without being affected by the nitrogen affinity of the center metal. Further, the above amines may be employed singly or in mixtures of two or more in any ratio.

Chain or cyclic secondary amines may be employed as the above secondary amine. The secondary amines denoted by general formula (5) below may be employed as a chain secondary amine.

General formula (5)

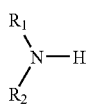

In general formula (5), each of $R_1$ and $R_2$ independently denotes a straight chain or branched chain alkyl group having 1 to 9 carbon atoms or an aryl group having 6 to 14 carbon atoms. In general formula (5), $R_1$ and $R_2$ may be identical to or different from each other.

Specific examples of the above secondary amine are: dimethylamine, diethylamine, dipropylamine, diisopropylamine, dibutylamine, dipentylamine, dihexylamine, diheptylamine, dioctylamine, dinonylamine, N-methylaniline, N-ethylaniline, piperidine, morpholine, and diphenylamine.

As set forth above, amines are thought to form a complex with a metal component in a solvent. This complex is thought to accelerate the reaction with the starting compound denoted by general formula (1) or (2) due to the presence of a suitable amount of space around the metal. Thus, from the perspective of ensuring adequate space around the metal, the use of a stereoscopically small secondary amine in the reaction is desirable. Examples of desirable secondary amines are those in which each of $R_1$ and $R_2$ independently denotes a methyl group, ethyl group, or propyl group. Specific examples are dimethylamine, diethylamine, dipropylamine, and cyclic secondary amines such as piperidines and morpholines.

Examples of these diamines are: ethylenediamine, N,N'-dimethylethylenediamine, N,N'-diethylethylenediamine, N-methylethylenediamine, N-methylpropanediamine, N,N'-dipropylethylenediamine, propanediamine, N,N'-dimethylpropanediamine, N,N'-diethylpropanediamine, and N,N'-dipropylpropanediamine. Of these, the preferred compounds are N,N'-dimethylethylenediamine, N,N'-dimethylpropanediamine, N-methylpropanediamine, and N-methylethylenediamine.

The above amines (secondary amines and diamines) may be employed in a quantity of 0.2 to 10.0 equivalents relative to the metal component. This quantity is desirably 0.5 to 4.0 equivalents relative to the metal component, with 2 equivalents being optimal for secondary amines and 1 equivalent being optimal for diamines.

The above reaction may be conducted in the copresence of the above amine and an ammonium salt. Ammonium salts that are suitable for use are ammonium benzoate, ammonium acetate, ammonium carbonate, and ammonium sulfate. Of these, ammonium benzoate and ammonium acetate are preferred. These ammonium salts may be employed singly or in combinations of two or more.

The quantity of the above ammonium salt employed may be 0.2 to 10.0 equivalents relative to the metal component. This quantity is preferably 0.5 to 4.0 equivalents, more preferably 2 equivalents, relative to the metal component.

Any of the generally known reaction solvents may be employed so long as they are stable. Examples are: alcohols such as hexanol and diethylene glycol; amide solvents such as N,N-dimethylformamide, N,N-dimethylacetamide, N,N-diethylacetamide, and N-methylpyrrolidone; imide solvents such as N,N'-dimethylimidazolidinone, and N,N'-dimethylpyrimidinone; hexamethylphosphotriamide; and dimethylsulfoxide. From the perspective of enhancing the yield, the use of alcohols, amide solvents, and imide solvents is desirable. Of these, diethylene glycol, N-methylpyrrolidone, N,N'-dimethylimidazolidinone, N,N'-dimethyltetrahydropyrimidinone, N,N-dimethylformamide, N,N-dimethylacetamide, N,N-diethylformamide, and N,N-diethylacetamide are preferred. These solvents may be employed singly or in combinations of two or more in any ratio. The method of the present invention affords the advantage of making it possible to conduct the reaction without a halogen solvent.

The reaction temperature can be suitably set based on the starting materials employed, the type of solvent, and the like; for example, the reaction may be conducted at 50 to 200 degree Celsius, preferably 90 to 160 degree Celsius. The reaction is desirably conducted with stirring. The reaction period may be suitably adjusted based on the progress of the reaction.

In the present invention, the above-described reaction yields the phthalocyanine compound denoted by general formula (3) below.

General formula (3)

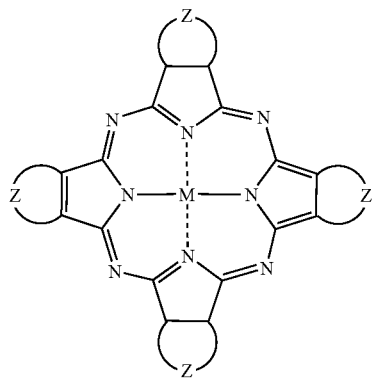

In general formula (3), Z is one defined as in general formulas (1) and (2), and M denotes a metal atom comprised in the metal or metal compound mentioned above.

Following the reaction, the desired product can be obtained by distilling off the solvent or adding a poor solvent relative to the phthalocyanine compound to the reaction solution to recover the precipitate that forms by filtration. Formation of the desired product may be confirmed by a known method such as NMR, mass spectrometry, or elemental analysis.

The phthalocyanine compound thus obtained may be employed in inkjet ink, sublimation transfer color copying, ink dyes, color filters, printing, optical recording media, and various other applications.

EXAMPLES

The present invention will be described in detail below based on examples. However, the present invention is not limited to the examples.

Example 1

Center Metal: Zinc

A 30 g quantity (120 mmoles) of 3-isobutylsulfonyl-1,2-dicyanobenzene, 3.1 mL (30.0 mmoles) of N,N-diethylamine, 2.4 g (30.0 mmoles) of ammonium acetate, and 7 g (30 mmoles) of zinc (II) bromide were dissolved in 30 mL of N-methylpyrrolidone and the mixture was stirred for 5 hours with heating at 115 degree Celsius. The mixture was then cooled to room temperature and 110 mL of N-methylpyrrolidone, 80 mL of water, and 80 mL of methanol were added. The blue reaction precipitate was recovered by filtration, yielding 22.8 g of the desired phthalocyanine compound. The yield was 71.7 percent.

Example 2

Center Metal: Cobalt

A 10 g quantity (40 mmoles) of 3-1-sulfopropylsulfonyl-1,2-dicyanobenzene sodium, 0.79 mL (7.43 mmoles) of N,N'-dimethylethylenediamine, and 0.96 g (0.73 mmole) of cobalt (II) chloride were dissolved in 20 mL of N-methylpyrrolidone and the mixture was stirred for 5 hours with heating at 118 degree Celsius. The mixture was then cooled to room temperature and 27 mL of N-methylpyrrolidone, 29 mL of water, and 27 mL of methanol were added. The blue reaction precipitate was recovered by filtration, yielding 8.64 g of the desired phthalocyanine compound. The yield was 82.8 percent.

Example 3

Center Metal: Nickel

A 10 g quantity (40 mmoles) of 3-1-sulfopropylsulfonyl-1,2-dicyanobenzene sodium, 0.79 mL (7.43 mmoles) of N,N'-dimethylethylenediamine, and 0.96 g (0.73 mmole) of nickel (II) chloride were dissolved in 20 mL of N-methylpyrrolidone and the mixture was stirred for 5 hours with heating at 115 degree Celsius. The mixture was then cooled to room temperature and 27 mL of N-methylpyrrolidone, 29 mL of water, and 27 mL of methanol were added. The blue reaction precipitate was recovered by filtration, yielding 2.35 g of the desired phthalocyanine compound. The yield was 84.5 percent.

Example 4

Center Metal: Manganese

A 30 g quantity (120 mmoles) of 3-1-sulfopropylsulfonyl-1,2-dicyanobenzene sodium, 0.79 mL (7.43 mmoles) of N,N'-dimethylethylenediamine, and 0.93 g (0.73 mmole) of manganese (II) chloride were dissolved in 20 mL of N-methylpyrrolidone and the mixture was stirred for 5 hours with heating at 115 degree Celsius. The mixture was then cooled to room temperature and 27 mL of N-methylpyrrolidone, 29 mL of water, and 27 mL of methanol were added. The green reaction precipitate was recovered by filtration, yielding 9.30 g of the desired phthalocyanine compound. The yield was 88.2 percent.

Example 5

Center Metal: Iron

A 10 g quantity (40 mmoles) of 3-1-sulfopropylsulfonyl-1,2-dicyanobenzene sodium, 0.79 mL (7.43 mmoles) of N,N'-dimethylethylenediamine, and 0.94 g (0.73 mmole) of ferrous chloride were dissolved in 20 mL of N-methylpyrrolidone and the mixture was stirred for 5 hours with heating at 115 degree Celsius. The mixture was then cooled to room temperature and 27 mL of N-methylpyrrolidone, 29 mL of water, and 27 mL of methanol were added. The green reaction precipitate was recovered by filtration, yielding 9.10 g of the desired phthalocyanine compound. The yield was 87.3 percent.

Example 6

Center Metal: Copper

A 5 g quantity (20 mmoles) of 3-isobutylsulfonyl-1,2-dicyanobenzene, 1.1 mL (13.7 mmoles) of diethylamine, and 0.67 g (5 mmoles) of cupric chloride were dissolved in 20 mL of ethylene glycol and the mixture was stirred for 3 hours with heating at 115 degree Celsius. The mixture was then cooled to room temperature and 0.58 mL of concentrated hydrochloric acid, 13.3 mL of water, and 13.3 mL of methanol were added. The blue reaction precipitate was recovered by filtration, yielding 5.09 g of the desired phthalocyanine compound. The yield was 95.7 percent.

Example 7

Center Metal: Zinc

A 10 g quantity (40 mmoles) of 3-isobutylsulfonyl-1,2-dicyanobenzene, 16.7 mL (80 mmoles) of HMDS, 1.0 mL (9.7 mmoles) of N,N-diethylamine, and 2.3 g (10 mmoles) of zinc (II) bromide were dissolved in 20 mL of N-methylpyrrolidone and the mixture was stirred for 5 hours with heating at 115 degree Celsius. The mixture was then cooled to room temperature and 27 mL of N-methylpyrrolidone, 27 mL of water, and 26 mL of methanol were added. The blue reaction precipitate was recovered by filtration, yielding 6.91 g of the desired phthalocyanine compound. The yield was 66.0 percent.

Example 8

Center Metal: Copper

A 5 g quantity (20 mmoles) of 3-isobutylsulfonyl-1,2-dicyanobenzene, 0.44 g (5.1 mmoles) of morpholine, and 0.67 g (5 mmoles) of cupric chloride were dissolved in 10 mL of N-methylpyrrolidone and the mixture was stirred for 3 hours with heating at 115 degree Celsius. The mixture was then cooled to room temperature and 13.3 mL of water and 13.3 mL of methanol were added. The blue reaction precipitate was recovered by filtration, yielding 4.66 g of the desired phthalocyanine compound. The yield was 83.9 percent.

Example 9

Center Metal: Nickel

A 5 g quantity (20 mmoles) of 3-isobutylsulfonyl-1,2-dicyanobenzene, 0.44 g (5.1 mmoles) of morpholine, and 0.65 g (5 mmoles) of nickel (II) chloride were dissolved in 10 mL of N-methylpyrrolidone and the mixture was stirred for 3 hours with heating at 115 degree Celsius. The mixture was then cooled to room temperature and 13.3 mL of water and 13.3 mL of methanol were added. The blue reaction precipitate was recovered by filtration, yielding 4.48 g of the desired phthalocyanine compound. The yield was 85.8 percent.

Example 10

Central Metal: Cobalt

A 5 g quantity (20 mmoles) of 3-isobutylsulfonyl-1,2-dicyanobenzene, 0.44 g (5.1 mmoles) of morpholine, and 0.65 g (5 mmoles) of cobalt (II) chloride were dissolved in 10 mL of N-methylpyrrolidone and the mixture was stirred for 3 hours with heating at 115 degree Celsius. The mixture was then cooled to room temperature and 13.3 mL of water and 13.3 mL of methanol were added. The blue reaction precipitate was recovered by filtration, yielding 5.00 g of the desired phthalocyanine compound. The yield was 94.3 percent.

Example 11

Center Metal: Cobalt

A 5 g quantity (20 mmoles) of 3-isobutylsulfonyl-1,2-dicyanobenzene, 0.85 g (10 mmoles) of piperidine, and 0.65 g (5 mmoles) of cobalt (II) chloride were dissolved in 10 mL of N-methylpyrrolidone and the mixture was stirred for 3 hours with heating at 115 degree Celsius. The mixture was then cooled to room temperature and 13.3 mL of water and 13.3 mL of methanol were added. The blue reaction precipitate was recovered by filtration, yielding 4.08 g of the desired phthalocyanine compound. The yield was 77.0 percent.

Example 12

Center Metal: Magnesium

A 5 g quantity (20 mmoles) of 3-isobutylsulfonyl-1,2-dicyanobenzene, 0.44 g (5.0 mmoles) of N,N'-dimethylethylenediamine, and 0.93 g (5 mmoles) of magnesium (II) bromide were dissolved in 5 mL of N-methylpyrrolidone and the mixture was stirred for 3 hours with heating at 150 degree Celsius. The mixture was then cooled to room temperature and 5 mL of NMP, 13.3 mL of water and 13.3 mL of methanol were added. The blue reaction precipitate was recovered by filtration, yielding 4.14 g of the desired phthalocyanine compound. The yield was 81.3 percent.

Example 13

Center Metal: Nickel

A 5 g quantity (20 mmoles) of 3-isobutylsulfonyl-1,2-dicyanobenzene, 0.51 g (5.0 mmoles) of N,N'-dimethylpropanediamine, and 0.65 g (5 mmoles) of nickel (II) chloride were dissolved in 10 mL of N-methylpyrrolidone and the mixture was stirred for 3 hours with heating at 115 degree Celsius. The mixture was then cooled to room temperature and 13.3 mL of water and 13.3 mL of methanol were added. The blue reaction precipitate was recovered by filtration, yielding 4.29 g of the desired phthalocyanine compound. The yield was 80.9 percent.

Example 14

Center Metal: Cobalt

A 5 g quantity (20 mmoles) of 3-isobutylsulfonyl-1,2-dicyanobenzene, 0.39 g (5.0 mmoles) of N-methylpropanediamine, and 0.65 g (5 mmoles) of cobalt (II) chloride were dissolved in 10 mL of N-methylpyrrolidone and the mixture was stirred for 3 hours with heating at 115 degree Celsius. The mixture was then cooled to room temperature and 13.3 mL of water and 13.3 mL of methanol were added. The blue reaction precipitate was recovered by filtration, yielding 4.35 g of the desired phthalocyanine compound. The yield was 82.0 percent.

Comparative Example 1

Center Metal: Zinc

A 30 g quantity (120 mmoles) of 3-isobutylsulfonyl-1,2-dicyanobenzene, 4.2 mL (30 mmoles) of triethylamine, and 7 g (30 mmoles) of zinc (II) bromide were dissolved in 30 mL of N-methylpyrrolidone and the mixture was stirred for 5 hours with heating at 115 degree Celsius. The mixture was then cooled to room temperature and 110 mL of N-methylpyrrolidone, 80 mL of water, and 80 mL of methanol were added. The blue reaction precipitate was recovered by filtration, yielding 1.91 g of the desired phthalocyanine compound. The yield was 6.0 percent.

Comparative Example 2

Center Metal: Copper

A 5 g quantity (20 mmoles) of 3-isobutylsulfonyl-1,2-dicyanobenzene and 0.67 g (5 mmoles) of cupric chloride were dissolved in 20 mL of diethylene glycol and the mixture was stirred for 6 hours with heating at 115 degree Celsius. The mixture was then cooled to room temperature and 0.58 mL of concentrated hydrochloric acid, 13.3 mL of water, and 13.3 mL of methanol were added. The blue reaction precipitate was recovered by filtration, yielding 3.57 g of the desired phthalocyanine compound. The yield was 67.1 percent.

Comparative Example 3

Center Metal: Zinc

A 10 g quantity (40 mmoles) of 3-isobutylsulfonyl-1,2-dicyanobenzene, 16.7 mL (80 mmoles) of FIMDS, and 2.3 g (10 mmoles) of zinc (II) bromide were dissolved in 20 mL of N-methylpyrrolidone and the mixture was stirred for 5 hours with heating at 115 degree Celsius. The mixture was then cooled to room temperature and 27 mL of N-methylpyrrolidone, 27 mL of water, and 26 mL of methanol were added. The blue reaction precipitate was recovered by filtration, yielding 3.86 g of the desired phthalocyanine compound. The yield was 36.3 percent.

From the above results, it will be clear that the method of the present invention makes it possible to obtain with high yield a phthalocyanine compound containing a desired center metal irrespective of the nitrogen affinity of the center metal. Further, the method of the present invention does not require a strong base and the reaction is conducted at relatively low temperature and in a relatively short period, thereby making it an advantageous method for synthesizing phthalocyanines containing a variety of substituents. The method of the present invention is also advantageous in that it simplifies the manufacturing process and is economical.

INDUSTRIAL APPLICABILITY

The present invention permits the efficient and economical manufacturing of a phthalocyanine compound having a desired center metal irrespective of the nitrogen affinity of the center metal.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The invention claimed is:

1. A method of preparing a phthalocyanine compound denoted by general formula (3), which comprises conducting a reaction of a compound denoted by general formula (1) or (2) with a metal and/or metal compound in a solvent in the presence of a secondary amine and/or diamine and the copresence of an ammonium salt to obtain the phthalocyanine compound denoted by general formula (3):

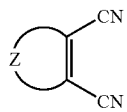

General formula (1)

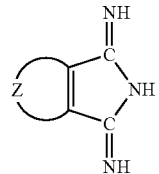

General formula (2)

wherein in general formulae (1) and (2), Z denotes an organic group forming a six-membered cyclic aromatic structure with two carbon atoms bonded to Z, wherein the six-membered cyclic aromatic structure is selected from the group consisting of a benzene ring, a naphthalene ring, a pyridine ring, and a pyridazine ring, each of which may be substituted:

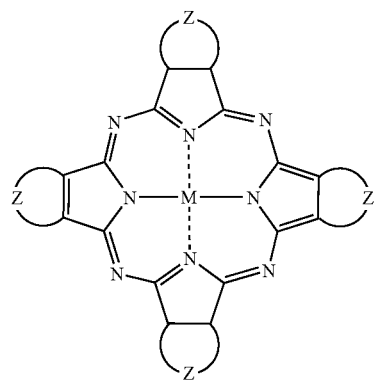

General formula (3)

wherein in general formula (3), Z has the same meaning as in general formulae (1) and (2), and M denotes a metal atom selected from the group consisting of Li, Be, Na, Mg, K, Ca, Sc, Ti, V, Cr, Mn, Fe, Co, Ni, Cu, and Zn.

2. The method of claim 1, wherein M in general formula (3) is Li, Be, Na, Mg, Mn, Fe, Co, Ni, Cu or Zn.

3. The method of claim 2, wherein M in general formula (3) is Mg, Mn, Fe, Co, Ni, Cu or Zn.

4. The method of claim 1, wherein the compound denoted by general formula (1) is a compound denoted by general formula (4):

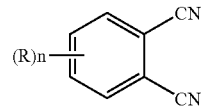

General formula (4)

wherein in general formula (4), R denotes a hydrogen atom or a substituent selected from the group consisting of an alkoxy group, an aryloxy group, a heterocyclic oxy group, an alkylsulfonyl group, an arylsulfonyl group, a heterocyclic sulfonyl group, an alkylthiol group, an arylthiol group, a heterocyclic thiol group or a sulfamoyl group, the heterocyclic moiety in each of the heterocyclic oxy group, the heterocyclic sulfonyl group and the heterocyclic thiol group being selected from the group consisting of a 2-furyl group, a 2-thienyl group, a 2-pyridyl group, a 4-pyridyl group, a 2-pyrimidinyl group, a 2-benzothiazolyl group, a pyridinio group, an imidazolio group, a quinolinio group, and an isoquinolinio group, n is an integer ranging from 1 to 4, and when n is an integer ranging from 2 to 4 such that more than one R is present, the plural Rs may be identical to or different from each other.

5. The method of claim 1, wherein the secondary amine is at least one selected from the group consisting of dimethylamine, diethylamine, dipropylamine, diisopropylamine, dibutylamine, dipentylamine, dihexylamine, diheptylamine, dioctylamine, dinonylamine, N-methylaniline, N-ethylaniline, piperidine, morpholine and diphenylamine.

6. The method of claim 1, wherein the secondary amine is at least one selected from the group consisting of dimethylamine, diethylamine, piperidine, morpholine and dipropylamine.

7. The method claim of 1, wherein the diamine is selected from the group consisting of N,N'-dimethylethylenedia, N-methylethylenediamine, N-methylpropanediamine and N,N'-dimethylpropanediamine.

8. The method of claim 1, wherein the ammonium salt is ammonium benzoate and/or ammonium acetate.

9. The method of claim 1, wherein the solvent is at least one selected from the group consisting of alcohols, amide solvents and imide solvents.

10. The method of claim 9, wherein the solvent is at least one selected from the group consisting of diethylene glycol, N-methylpyrrolidone, N,N'-dimethylimidazolidinone, N,N'-dimethyltetrahydropyrimidinone, N,N-dimethylformamide, N,N-dimethylacetamide, N,N-diethylformamide and N,N-diethylacetamide.

* * * * *